United States Patent
Kumar

(10) Patent No.: US 10,980,443 B2
(45) Date of Patent: Apr. 20, 2021

(54) CONSCIOUS RHYTHMIC BREATHING SENSING

(71) Applicant: Sai Kumar, Dallas, TX (US)

(72) Inventor: Sai Kumar, Dallas, TX (US)

( * ) Notice: Subject to any disclaimer, the term of this patent is extended or adjusted under 35 U.S.C. 154(b) by 781 days.

(21) Appl. No.: 15/614,166

(22) Filed: Jun. 5, 2017

(65) Prior Publication Data
US 2017/0265777 A1 Sep. 21, 2017

Related U.S. Application Data

(63) Continuation-in-part of application No. 13/711,528, filed on Dec. 11, 2012, now Pat. No. 10,251,434.

(60) Provisional application No. 62/345,898, filed on Jun. 6, 2016.

(51) Int. Cl.
*A61B 5/087* (2006.01)
*A61B 5/00* (2006.01)

(52) U.S. Cl.
CPC ............. *A61B 5/087* (2013.01); *A61B 5/486* (2013.01); *A61B 5/6819* (2013.01); *A61B 5/6838* (2013.01); *A61B 5/002* (2013.01); *A61B 5/0878* (2013.01)

(58) Field of Classification Search
CPC ..... A61B 5/0803; A61B 5/087; A61B 5/0876; A61B 5/09; A61B 5/097; A61B 5/486; A61B 5/6819; A61B 5/6838
See application file for complete search history.

(56) References Cited

U.S. PATENT DOCUMENTS

| | | | |
|---|---|---|---|
| 4,781,686 A | 11/1988 | Erickson | |
| 5,203,343 A | 4/1993 | Axe et al. | |
| 8,322,340 B2 | 12/2012 | Talmon | |
| 2006/0270941 A1* | 11/2006 | Xie | A61B 5/087 600/529 |
| 2009/0277459 A1 | 11/2009 | Al-Zeir | |
| 2010/0268131 A1 | 10/2010 | Efthimiou | |
| 2012/0203128 A1* | 8/2012 | Levison | A61B 5/0878 600/537 |
| 2014/0058733 A1 | 2/2014 | Voorhees et al. | |
| 2014/0275930 A1* | 9/2014 | Rich | A61B 5/02427 600/383 |
| 2016/0029922 A1* | 2/2016 | Bar-Lev | A61B 5/6819 600/324 |
| 2016/0150981 A1* | 6/2016 | Baker | G06F 19/00 600/479 |

* cited by examiner

*Primary Examiner* — Thaddeus B Cox
(74) *Attorney, Agent, or Firm* — MP Patents, LLC

(57) ABSTRACT

A device for increasing a user's awareness of his or her breathing includes a clip configured to attach to a user's nose, a hinge connected to the clip, an air deflection plate pivotably connected to the hinge and one or more sensors coupled with the air deflection plate. The air deflection plate is configured to pivot relative to the clip to at least partially deflect air flow into or out of a nostril while the air deflection plate is exterior to the nostril and the clip is attached to the user's nose. The one or more sensors are configured to sense data pertaining to the user's breathing through the nostril. A method for increasing breathing awareness includes, in response to air flow across an air deflection plate pivotably coupled with a clip gripping a user's nose, receiving breathing data with one or more sensors coupled with the air deflection plate.

14 Claims, 7 Drawing Sheets

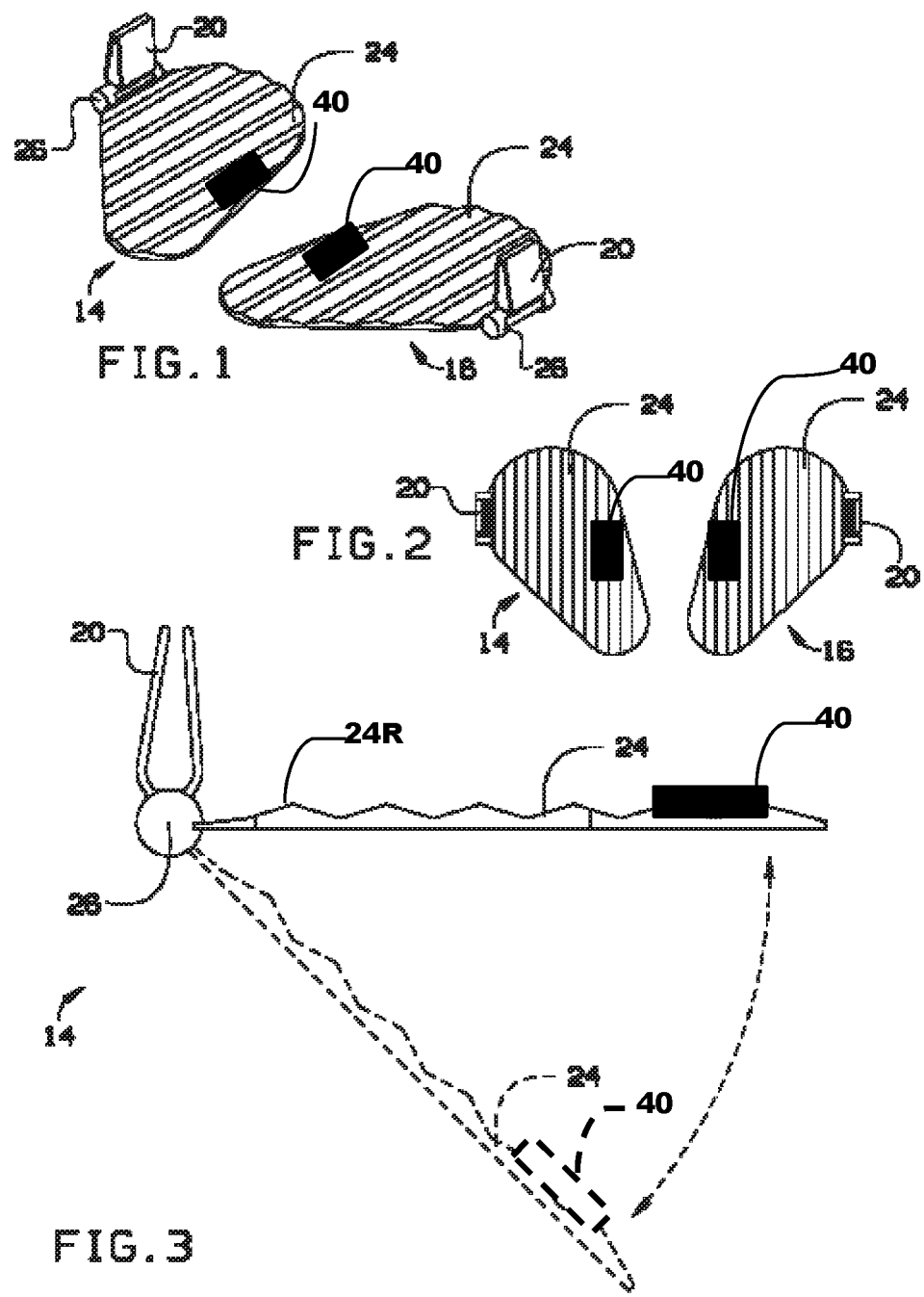

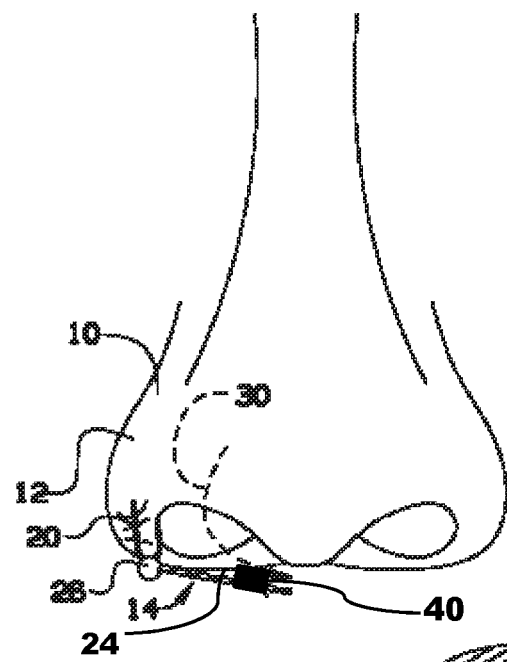
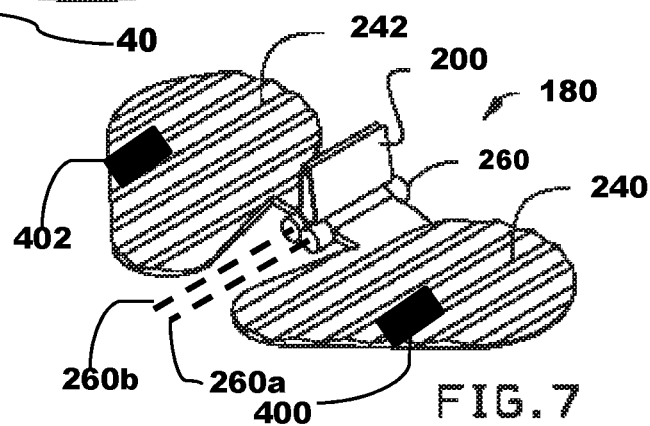
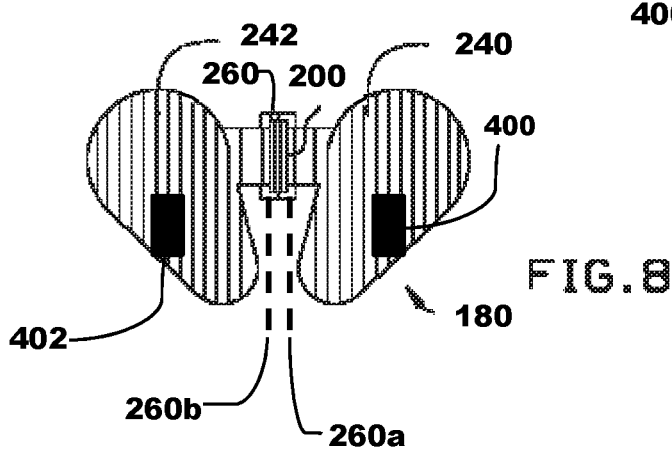

CONSCIOUS RHYTHMIC BREATHING SENSING

CROSS-REFERENCE TO RELATED APPLICATIONS

This application claims the priority benefit of U.S. Provisional Application No. 62/345,898 filed on Jun. 6, 2016 and is a continuation-in-part of U.S. Non-Provisional application Ser. No. 13/711,528, now U.S. Pat. No. 10,251,434, filed on Dec. 11, 2012 both of which are incorporated herein by reference in their entirety.

SUMMARY

The disclosure seeks to provide, in part, a system for increased breathing awareness. The system includes a first clip configured to grip a user's nose; a first air deflection plate pivotably coupled with the first clip by a first hinge and configured to pivot relative to the first clip and to at least partially deflect air flow from or into a nostril of the user's nose with the first clip gripping the user's nose and the first air deflection plate exterior to the nostril; one or more sensors coupled with the first air deflection plate and configured to sense breathing and transmit data resulting from the sensed breathing; and a mobile computing device programmed to receive and process data transmitted by the one or more sensors into breathing feedback and to present the breathing feedback to an output of the mobile computing device.

The system may also include a second air deflection plate pivotably coupled with the first clip by a second hinge and configured to at least partially deflect air flow from or into a second nostril with the first clip gripping the user's nose and the second air deflection plate exterior to the nostril. The one or more sensors are also configured to sense breathing through the second nostril.

The first and/or second air deflection plate of the system may include an irregular surface.

The first and/or second air deflection plate of the system may include a corrugated surface.

The first and/or second air deflection plate of the system may be configured to produce a sound in response to a user exhaling or inhaling.

The first and/or second air deflection plate of the system may also be configured to produce mechanical waves of pressure and displacement in air flow deflected by the first and/or second air deflection plate.

The mechanical waves may have a frequency in the range of from about 20 Hz to about 20,000 Hz.

The one or more sensors of the system may be coupled to an upper surface of the first and/or second air deflection plate.

The one or more sensors of the system may be coupled to a lower surface of the first and/or second air deflection plate.

The one or more sensors of the system may be coupled to upper and lower surfaces of the first and/or second air deflection plate.

The one or more sensors of the system may be embedded within the first and/or second air deflection plate.

The disclosure also seeks to provide, in part, a device for increased breathing awareness including a clip configured to grip a user's nose; a first air deflection plate pivotably coupled with the clip by a first hinge and configured to at least partially deflect air flow from or into a first nostril with the clip gripping the user's nose; a second air deflection plate pivotably coupled with the clip by a second hinge and configured to at least partially deflect air flow from or into a second nostril with the clip gripping the user's nose; and one or more sensors coupled with at least one of the first air deflection plate and the second air deflection plate, the one or more sensors being configured to sense air flow through at least one of the first nostril and the second nostril.

The first hinge and the second hinge of the device for increased breathing awareness may be other than living hinges.

The first hinge and the second hinge of the device for increased breathing awareness may be barrel hinges.

The first air deflection plate of the device may configured for pivoting about a first axis and the second air deflection plate of the device may be configured for pivoting about a second axis parallel with and spaced apart from the first axis.

The clip, the first air deflection plate, the second air deflection plate, the first hinge and the second hinge may be arranged such that, with the clip gripping a user's nose, the first air deflection plate is configured to pivot relative to the clip about a first axis exterior to the user's first nostril and the second air deflection plate is configured to pivot relative to the clip about a second axis exterior to the user's second nostril.

The clip of the device for increased breathing awareness may further include gripping arms configured to grip a portion of a user's nose.

The disclosure also seeks to provide, in part, a device for increasing a user's awareness of his or her breathing which includes a clip configured to attach to a user's nose; a first hinge connected to the clip; a first air deflection plate pivotably connected to the first hinge, the first air deflection plate configured to pivot relative to the clip, the first air deflection plate further configured to at least partially occlude a first nostril while the first air deflection plate is exterior to the nostril and the clip is attached to the user's nose; and one or more sensors coupled with the first air deflection plate and configured to sense data pertaining to the user's breathing through the first nostril.

The disclosure also seeks to provide, in part, a method for increasing breathing awareness including, in response to air flow across an air deflection plate pivotably coupled with a clip gripping a user's nose, receiving breathing data with one or more sensors coupled with the air deflection plate; transmitting the breathing data to a computing device; processing the breathing data with the computing device to yield breathing feedback; and presenting the breathing feedback to an output of the computing device.

Presenting the breathing feedback may further include presenting one or more of average breathing volume, current breathing rate, average breathing rate, lung capacity, percentage of oxygen intake, comparisons between current breathing volume and previous or average breathing volume and comparisons between breathing rate and previous or average breathing rate.

BRIEF DESCRIPTION OF THE FIGURES

The summary above, as well as the following detailed description of illustrative embodiments, is better understood when read in conjunction with the appended drawings. For the purpose of illustrating the present disclosure, example constructions of the disclosure are shown in the drawings. However, the present disclosure is not limited to specific methods and instrumentalities disclosed herein. Moreover, those having ordinary skill in the art will understand that the drawings are not to scale. Wherever possible, like elements have been indicated by identical numbers.

Embodiments of the present disclosure will now be described, by way of example only, with reference to the following diagrams.

Figure 4:
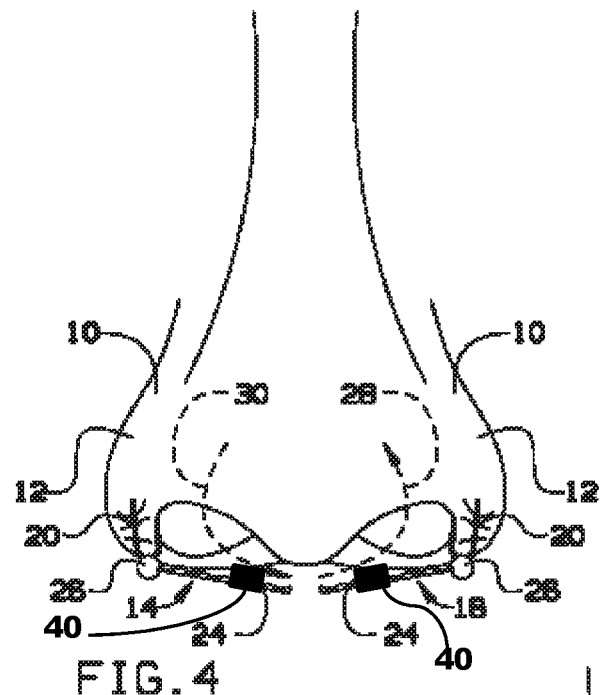
Figure 5:
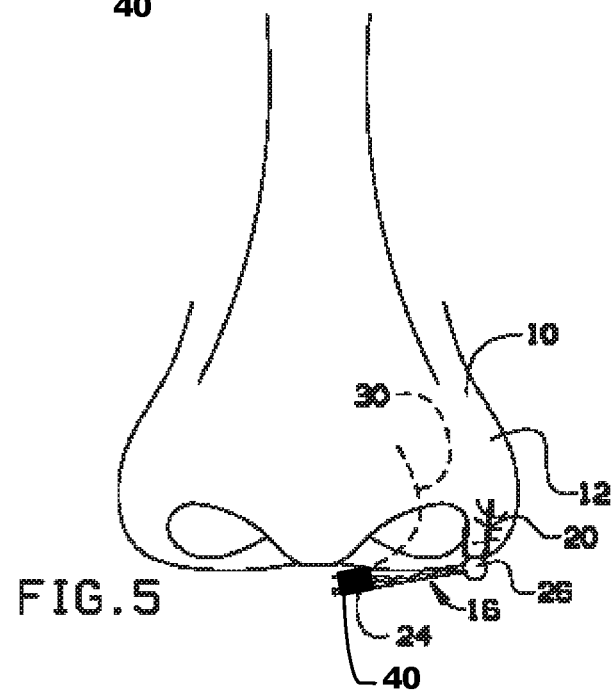
Figure 9:
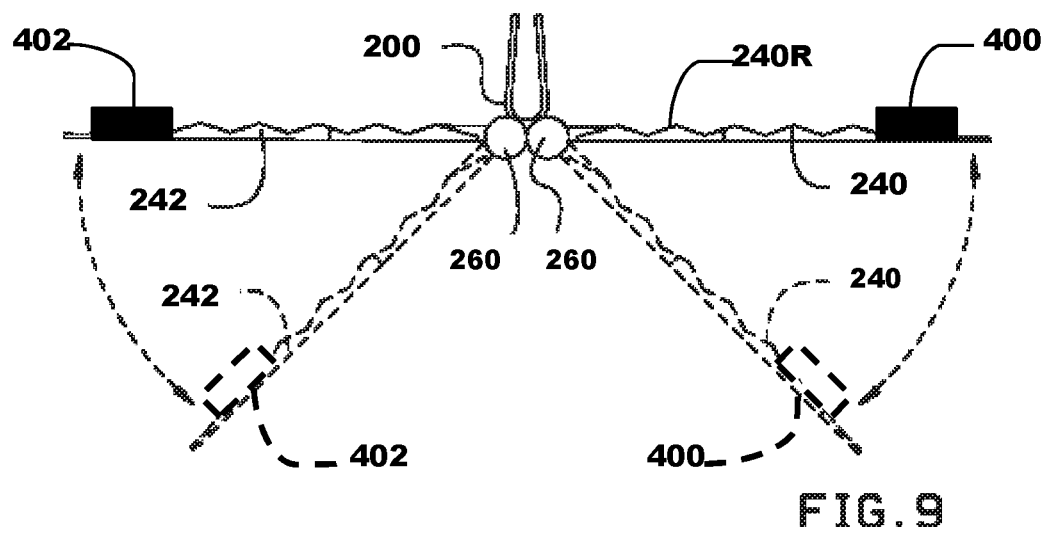
Figure 10:
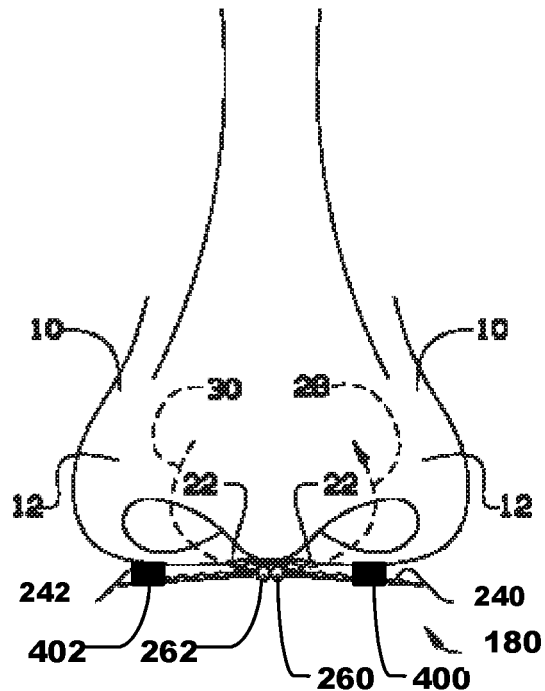
Figure 11:
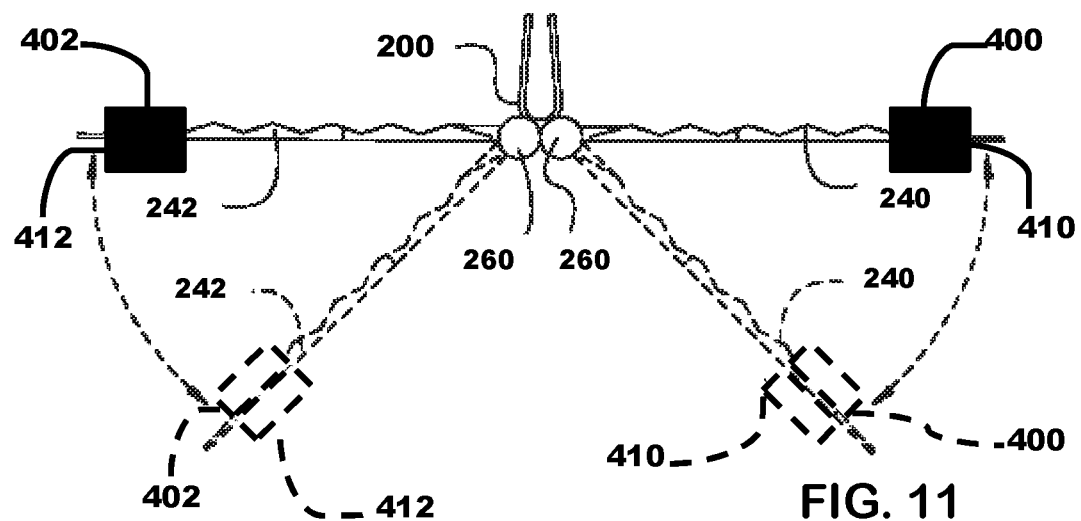
Figure 12:
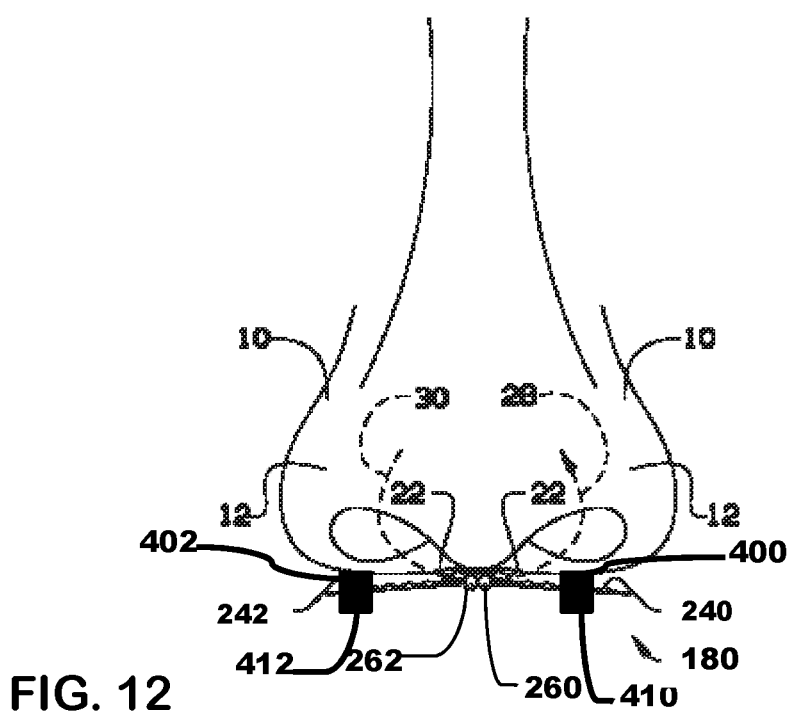
Figure 13:
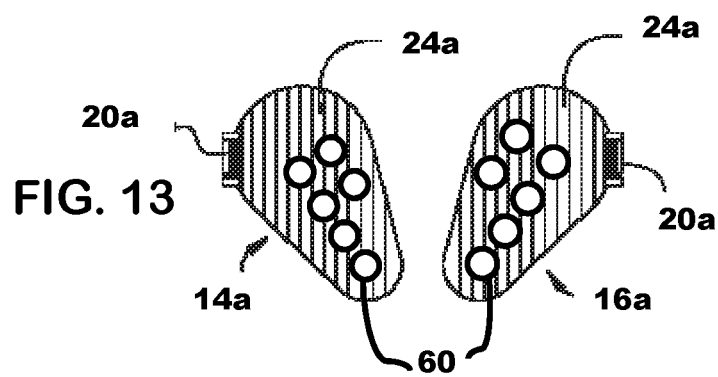
Figure 14:
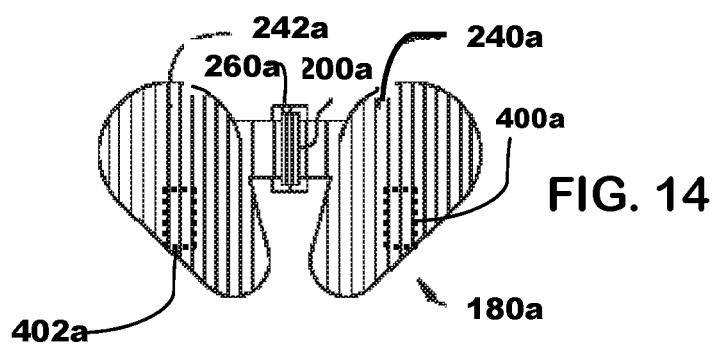
Figure 15:
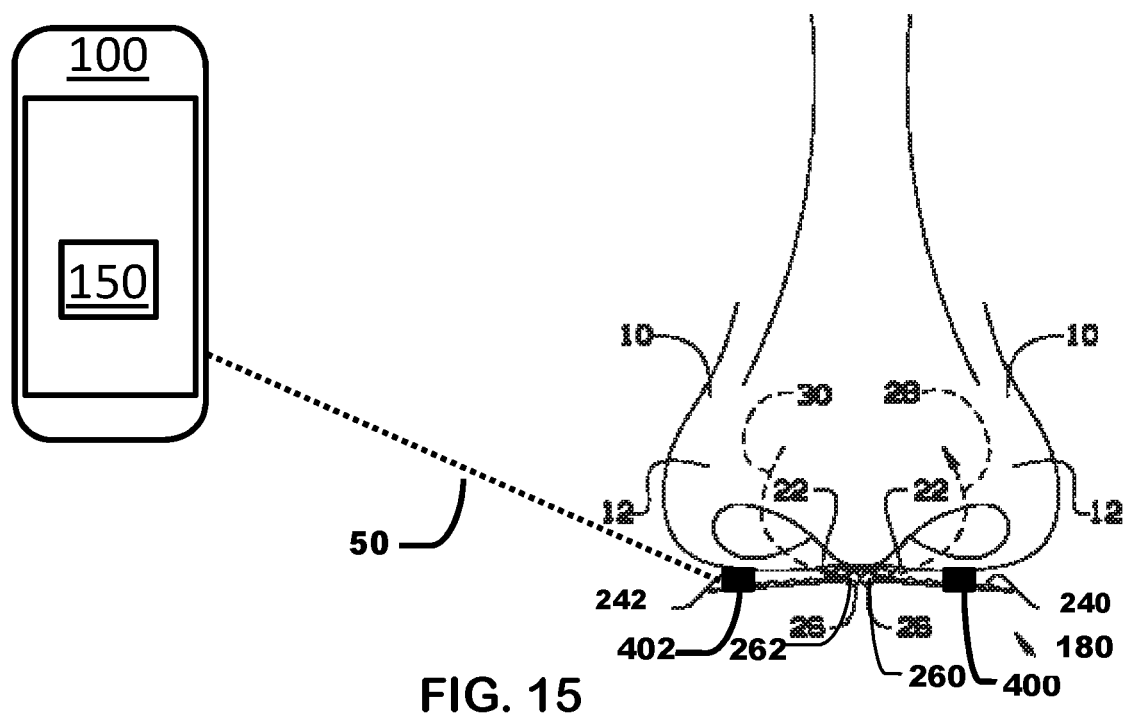

The accompanying drawings, which are included to provide a further understanding of the present disclosure, are incorporated in and constitute a part of this specification, illustrate aspects of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings:

FIG. 1 shows an example conscious rhythmic breathing sensing device, according to a first embodiment of the present disclosure;

FIG. 2 shows a top view of the example device of FIG. 1;

FIG. 3 shows a pivoting motion of the example device of FIG. 1;

FIGS. 4, 5, and 6 show the example device of FIG. 1 in relation to a user's nose;

FIG. 7 shows an example conscious rhythmic breathing sensing device, according to a second embodiment of the present disclosure;

FIG. 8 shows a top view of the example device of FIG. 7;

FIG. 9 shows a pivoting motion of the example device of FIG. 7;

FIG. 10 shows the example device of FIG. 7 in relation to a user's nose;

FIG. 11 shows an example conscious rhythmic breathing sensing device in accordance with a third embodiment in which sensors are located on both the upper and lower surfaces of air deflection plates;

FIG. 12 shows the example conscious rhythmic breathing sensing device in accordance with the third embodiment of FIG. 11 in relation to a user's nose;

FIG. 13 shows an example conscious rhythmic breathing sensing device including one or more perforations;

FIG. 14 shows an example conscious rhythmic breathing sensing device including sensors embedded in deflection plates; and FIG. 15 shows an example conscious rhythmic breathing sensing device in communication with an example mobile computing device.

DETAILED DESCRIPTION

The aspects of the present disclosure and the various features and advantageous details thereof are explained more fully with reference to the non-limiting aspects and examples that are described and/or illustrated in the accompanying drawings and detailed in the following description. It should be noted that the features illustrated in the drawings are not necessarily drawn to scale, and features of one aspect may be employed with other aspects as the skilled artisan would recognize, even if not explicitly stated herein. Descriptions of well-known components and processing techniques may be omitted so as to not unnecessarily obscure the aspects of the present disclosure. The examples used herein are intended merely to facilitate an understanding of ways in which the present disclosure may be practiced and to further enable those of skill in the art to practice the aspects of the present disclosure. Accordingly, the examples and aspects herein should not be construed as limiting the scope of the present disclosure, which is defined solely by the appended claims and applicable law. Moreover, it is noted that like reference numerals represent similar parts throughout the drawings.

Breathing exercises, such as, e.g., pranayama, are commonly used in many religious, spiritual, and meditation practices to focus an individual's mind on his body and the present moment. By focusing on his/her breathing and the present, the individual's mind may release or let go of stress, worries, anxiety, anger, and other emotions. Individuals with busy lives and hectic schedules may forget or simply not think to put these types of practices to use in their everyday lives, such as when, e.g., using a computer, driving a car, waiting in line, and so on. Accordingly, there is a need for "yoga on the go."

FIG. 1 shows an example conscious rhythmic breathing sensing device, according to an aspect of the present disclosure, and FIG. 2 shows a top view of the example device of FIG. 1. The device may help the user to enhance his or her awareness of his or her breathing pattern and to engage in conscious and rhythmic breathing. This type of breathing, which may be slow and rhythmic, may be similar to breathing that takes place during yoga or other relaxation practices. By practicing this type of breathing more frequently in his daily life, the user of the device may, for example, focus more on the present moment, reduce stress, increase relaxation, and so on.

Referring to FIG. 1, an example conscious rhythmic breathing sensing device may include a single device or a pair of devices. A pair may include a right nostril device 14 and a left nostril device 16. An individual conscious rhythmic breathing sensing device may include an air deflection plate 24. Air deflection plate 24 includes a width between first and second sides and a length between first and second ends. Any of a variety of shapes may be defined by the length and the width of air deflection plate 24. In one example, the plate takes a wing or teardrop shape. The air deflection plate 24 may be substantially solid with no holes or perforations as viewed in FIG. 1, such that air deflection plate 24 is not readily permeated by air or other fluids. In another example, the air deflection plate may include holes or perforations as described below.

Referring to FIGS. 1-3, air deflection plate 24 may be coupled with a clip 20 by a hinge 26 at a first side of the air deflection plate 24. In an example, hinge 26 enables relative pivoting between air deflection plate 24 and clip 20 about an axis parallel to the length and perpendicular to the width of the air deflection plate 24. Pivoting of air deflection plate 24 allows the user to adjust the angle thereof for comfortable breathing. In an example, hinge 26 is not a living hinge. In an example, hinge 26 is a barrel hinge. The air deflection plate 24 may have an irregular or corrugated upper surface, an irregular or corrugated lower surface, or both. In an example, air deflection plate 24 may include one corrugated surface and one non-corrugated or smooth surface. In an example, a corrugated surface may include parallel ridges 24R extending in a single direction. The irregular or corrugated surface may assist with making a user more aware of his breathing, as discussed below.

Further, air deflection plate 24 may be provided with sensors 40 coupled with an upper surface of deflection plate 24 of either left nostril device 16, right nostril device 14 or both and configured to detect air flow into and out of the user's nostril or nostrils. In an example, sensors 40, which may take any of a variety of shapes, may be adhered to or otherwise attached to a surface of air deflection plate 24. In a further example, sensors 40 may be embedded in deflection plate 24 (FIG. 14).

The sensors 40 coupled with one or more of deflection plates 24 are configured to sense and/or detect conditions at or around the user's nose and/or nostrils. Sensors 40 are additionally configured to provide data collected from or resulting from the sensed or detected conditions or data otherwise pertaining to the user's breathing. Such data may otherwise be recognized as conditions data, breathing data or sensor data. Example conditions include a breath or a flow such as respiratory flow. In an example, flow may be determined as a volume of air passing sensors 40. Example sensor types for use with the disclosed devices, systems and methods also include but are not limited to an accelerometer, a magnetometer, a motion sensor, a pressure sensor, a temperature sensor, a gyroscopic sensor, or a Global Positioning System (GPS) sensor and a combination of these. Sensors 40 may be used to measure and collect data related to surroundings of the user. Sensors 40 may also include, be coupled with or otherwise configured with a transmitter, receiver or transceiver enabling data to be transmitted from sensors 40, instructions or configurations to be received by sensors 40 or both.

FIG. 3 shows a pivoting motion of the example device of FIG. 1, and FIGS. 4-6 show the example device of FIG. 1 in relation to the nose 12 of a user 10. The clip 20 may be used to removably attach the device to the user's nose 12, for example, at the alar rim. In an example, clip 20 includes two gripping arms extending away from hinge 26 in the same direction and configured to grip a portion of a user's nose there between. For example, referring to FIG. 4, with clip 20 gripping to a user's nostril, hinge 26 is configured to enable air deflection plate 24 to be pivoted between a position in which the plate width extends away from the user's nostril to a position in which the plate width extends across a user's nostril. The device may be oriented so that the air deflection plate 24 at least partially covers or occludes the nostril. Deflecting the airflow may make the user more aware of his breathing and/or remind the user to practice conscious breathing techniques.

Further, air deflection plate 24 may be configured to produce or otherwise cause audible mechanical waves of pressure and displacement in air flow deflected by the deflection plate 24. In an example, mechanical waves have a frequency in the range of from about 20 Hz to about 20,000 Hz. As such, a sound, such as, for example, a gentle rustling or swishing sound may be audible when the user exhales, inhales, or both. Referring to FIGS. 4-6, exhalation is indicated generally by arrow 30, and inhalation is indicated generally by arrow 28. Production of the sound may be enhanced by an irregular or corrugated surface on the air deflection plate 24. Sound production may also be enhanced by one or more perforations in the air deflection plate 24. Along with sensors 40, the sound may serve to make the user more aware of his breathing and/or remind him or her to practice conscious breathing techniques.

It is estimated that 85% of people exhale from only one nostril at a time while inhaling from the other. Switching which nostril exhales and which nostril inhales may happen in a cyclical fashion, with a switch typically taking place every four hours or so. This time can vary between individuals and can be affected by factors such as, e.g., body position, nasal congestion, allergies, and so on. As a result, a user of a conscious rhythmic breathing sensing device may only need to use one device to cover one nostril at a time, as shown, e.g., in FIGS. 5 and 6.

FIG. 7 shows an example conscious rhythmic breathing sensing device, according to a second embodiment of the present disclosure, and FIG. 8 shows a top view of the example device of FIG. 7. Referring to FIGS. 7-10, a conscious rhythmic breathing sensing device may include two air deflection plates 240 and 242 coupled to central hinges 260. The hinges 260 may be coupled to a clip 200 for holding the device to a user's nose 10. In an example, hinges 260 includes first and second parallel and spaced apart pivot axes 260*a* and 260*b*. First air deflection plate 240 pivots relative to clip 200 about the first pivot axis 260*a* while second air deflection plate 242 pivots relative to clip 200 about the second pivot axis 260*b*. In an example, first and second pivot axes may lie entirely exterior to the user's nose during pivoting. In an example, a corrugated surface provided to the upper surface, the lower surface or both of plates 240 and 242 may include parallel ridges 240R extending in a single direction.

FIG. 9 shows a pivoting motion of the example device of FIG. 7. In an example, with clip 200 gripping a user's nose, first and second air deflection plates 240 and 242 may be pivoted into a lowered position away from the user's nostrils and towards each other or a first air deflection plate may be pivoted into a lowered position away from a first nostril while a second air deflection plate may remain in a raised position across a second nostril.

In an example, air deflection plates 240 and 242 may be pivoted from a position in which they are substantially coplanar in the raised position and extend across both of a user's nostrils to a lowered position in which they are substantially parallel and each plate is pivoted approximately 90 degrees away from its position across its respective nostril. In another example, the angle swept by a pivoting air deflection plate may be less than 90 degrees such as between 30 and 45 degrees such that pivoting both plates towards a lowered position does not yield parallelism between the deflection plates.

FIG. 10 shows the example device of FIG. 7 in relation to a user's nose. In use, clip 200 may removably attach to a user's septum between his or her nostrils 12 such that each deflection plate 240 and 242 extends across a nostril in a raised position. In another example, clip 200 may be removably attached to a user's nostril.

FIG. 11 shows pivoting motion of an example conscious rhythmic breathing sensing device in accordance with a third embodiment in which sensors 400 and 402 are coupled to the upper surface of air deflection plate 240 and 242 while sensors 410 and 412 are coupled to the lower surfaces of air deflection plates 240 and 242. In an example, sensors 400, 402, 410, and 412 may be adhered to or otherwise attached to a surface of air deflection plates 240 and 242 or may be embedded therein. In a further example, sensors 410 and 412 may be provided to lower surfaces of air deflection plates 24 while sensors 400 and 402 are omitted from the upper surfaces of deflection plates 240 and 242.

As with the embodiment of FIGS. 7-10, in an example with clip 200 gripping a user's septum, first and second air deflection plates 240 and 242 may be pivoted into a lowered position or a first plate may be pivoted into a lowered position while a second air deflection plate may remain in a raised position.

Sensors 400, 402, 410 and 412 may take any of a variety of shapes and may be adhered to or otherwise attached to a surface of air deflection plates 240 and/or 242. In a further example, sensors 400, 402, 410 and/or 412 may be embedded in deflection plates 240 and/or 242 (FIG. 14).

As with sensors 40, sensors 400, 402, 410 and 412 are configured to sense and/or detect conditions at or around the user's nose and/or nostrils and to provide data collected from or resulting from the sensed or detected conditions or data otherwise pertaining to the user's breathing. Also like sensors 40, sensors 400, 402, 410 and 412 may also include, be coupled with or otherwise configured with a transmitter, receiver or transceiver enabling data to be transmitted, instructions or configurations to be received or both. Similarly, example sensor types include but are not limited to an accelerometer, a magnetometer, a motion sensor, a pressure sensor, a temperature sensor, a gyroscopic sensor, or a Global Positioning System (GPS) sensor and a combination of these FIG. 12 shows the example conscious rhythmic breathing sensing device in accordance with the third embodiment of FIG. 11 in relation to a user's nose with air deflection plates 240 and 242 in a raised position. Clip 200 may removably attach to a user's septum and air deflection plates 240 and 242 may independently pivot relative to clip 200 between raised and lowered positions, as discussed above. It should be noted that coupling of sensors to both the upper and lower surfaces of deflection plates 240 and 242 is not limited to implementation solely in the example illustrated in FIGS. 11 and 12. In fact, multiple sensors may be implemented into each air deflection plate of any example device shown in FIGS. 1-10 as well.

In some examples, the sensors 40, 400, 402, 410 and 412 coupled with one or more of deflection plates 24, 240 and 242 may include a timer for including time-stamps with data sensed and/or collected by the sensors. Alternatively, the processor of a mobile computing device in communication with the sensors may provide system time as reference for including the time-stamps with the data.

In an example shown in FIG. 13, a conscious rhythmic breathing sensing device 14a or 16a having a clip 20a may include air deflection plates 24a having one or more holes or perforations 60. Holes or perforations 60 may be any shape, such as, e.g., circular, square, or rectangular and may vary in size and distribution throughout the plate. Aspects of the present disclosure may include an air deflection plate 24a that has most or all of its surface covered with perforations. Such an air deflection plate 24a may be regarded as an air deflection net or an air deflection mesh.

In an example shown in FIG. 14 a conscious rhythmic breathing sensing device 180a having a clip 200a and hinges 260a may include sensors 400a and 402a embedded in deflection plates 240a and 242a rather than coupled with their surface. Sensors 400a and 402a may take any of a variety of shapes and are configured to sense and/or detect conditions at or around the user's nose and/or nostrils as well as to provide data collected from or resulting from the sensed or detected conditions or data otherwise pertaining to the user's breathing. Also like sensors 40, sensors 400a and 402a may additionally include, be coupled with or otherwise configured with a transmitter, receiver or transceiver enabling data to be transmitted, instructions or configurations to be received or both. Sensors 400a and 402a may include but are not limited to an accelerometer, a magnetometer, a motion sensor, a pressure sensor, a temperature sensor, a gyroscopic sensor, or a Global Positioning System (GPS) sensor and a combination of these.

In an example method for increasing breathing awareness, a first air deflection plate is pivotably coupled with a clip by a first hinge. One or more sensors configured to receive breathing data are provided to the first air deflection plate. The clip is temporarily attached to a user's nose such that the first air deflection plate at least partially deflects air flow from or into a first nostril. Breathing data is received with the one or more sensors in response to the deflected air flow. At times during or after sensing and/or detecting conditions at or around the user's nose and/or nostrils, breathing data is transmitted to a mobile computing device by a transmission. The mobile computing device processes the breathing data to yield breathing feedback which may then be presented to an output of the computing device.

FIG. 15 shows an example conscious rhythmic breathing sensing device in wireless communication with an example mobile computing device 100, for example, through transmission 50. Data sent from or instructions or configurations sent to sensors 40, 400, 402, 410 and 412 may be transmitted in accordance with one or more wireless transmission protocols including but not limited to Bluetooth™ or WiFi™.

Example devices usable as mobile computing device 100 include, but are not limited to, mobile phones, smart telephones, Mobile Internet Devices (MIDs), tablet computers, Ultra-Mobile Personal Computers (UMPCs), phablet computers, Personal Digital Assistants (PDAs), web pads, handheld PCs, smart watches, wearable personal computers, laptop computers, and interactive entertainment devices, such as game consoles.

Mobile computing device 100 may include, but is not limited to including, a data memory, a computing hardware such as a processor, Input/Output (I/O) devices, a network interface, a configuration of sensors, a storage, and a system bus that operatively couples various components including the data memory, the processor, the I/O devices, the network interface, the sensors and the storage. The I/O devices include a display screen for presenting graphical images to a user of the mobile computing device.

The mobile computing device also includes a power source for supplying electrical power to the various components thereof. The power source may, for example, include a rechargeable battery.

The data memory optionally includes non-removable memory, removable memory, or a combination thereof. The non-removable memory, for example, includes Random-Access Memory (RAM), Read-Only Memory (ROM), flash memory, or a hard drive. The removable memory, for example, includes flash memory cards, memory sticks, or smart cards.

Embodiments of the present disclosure additionally provide a computer program product that includes a non-transitory or non-transient computer-readable storage medium storing computer-executable code in the form of conscious rhythmic breathing sensing software, a conscious rhythmic breathing sensing app or a conscious rhythmic breathing sensing application. Data memory of mobile computing device 100 stores an app, application, software or computer program product 150 associated with a conscious rhythmic breathing sensing service. The computer-executable code for conscious rhythmic breathing sensing, when executed, is configured to perform actions of the method for sensing, recording, and processing breathing data or other method increasing breathing awareness. As actions of such methods may be provided in different sequences, so the computer-executable code may be configured to provide a service having a different sequence of actions. In some examples, the code may be downloaded from a software application store, for example, from an "App store", to a data processing unit.

In some examples, the mobile computing device display screen may be a touch-sensitive display screen that is operable to receive tactile inputs from the user for interacting with the computer program product. These tactile inputs may, for example, include clicking, tapping, pointing, moving, pressing and/or swiping with a finger or a touch-sensitive object like a pen.

Additionally or alternatively, the I/O devices include a mouse or a joystick that is operable to receive inputs corresponding to clicking, pointing, and/or moving a pointer object on a graphical user interface. The I/O devices may also include a keyboard that is operable to receive inputs corresponding to pushing certain buttons on the keyboard. Additionally, the I/O devices may also include a microphone for receiving an audio input from the user, and a speaker for providing an audio output to the user.

In some examples, the sensors of mobile computing device 100 may include a GPS sensor for determining one or more absolute spatial positions of the user upon a surface of the Earth. In some examples, the mobile computing device sensors may include a timer for including the time-stamps with the data sensed and/or collected. Alternatively, the processor may provide system time as reference for including the time-stamps with the breathing data.

Moreover, the storage is a non-transient data storage medium. The computer program product, when executed on the processor, is optionally coupled to the storage, and is configured to substantially continuously record and update breathing data in the storage.

Furthermore, the network interface optionally allows mobile computing device 100 to upload the data to a server, for example, via a communication network. Additionally, the network interface may allow the mobile computing device to access the server to update the computer program product, to download one or more new computer program products and/or to exchange data or instructions with sensors 40, 400, 402, 410 and/or 412. Moreover, the network interface optionally allows the mobile computing device to communicate with other data processing units or other mobile computing devices, for example, via the communication network.

Through a mobile computing device and a conscious rhythmic breathing sensing application programmed to mobile computing device 100, the user will see at any point his/her breathing rate/frequency and breathing volume etc. When executed on the processor, the conscious rhythmic breathing sensing application is configured to resolve and integrate the outputs of the sensors 40 or 41 into useful information about at least one of pressure, percent of lung capacity used, temperature, humidity, stress and health.

The conscious rhythmic breathing sensing application may offer instantaneous and/or historical feedback on the user's mindful breathing practice. For example, the user may learn the depth of breaths, average breathing volume, current breathing rate, average breathing rate, ung capacity, percentage of oxygen intake, comparisons between current breathing volume and previous or average breathing volume, and/or comparisons between current breathing rate and previous or average breathing rate. In further examples, the feedback may include a numerical representation of current breathing volume adjacent to a numerical representation of average breathing volume or may include a numerical representation of a percentage of average breathing volume the current breathing volume represents.

In some examples, the application may be interfaced with the sensors 40 to control settings related thereto. For example, the frequency of data detection may be adjusted, data detection may be turned off or on, wireless communication protocols can be set and/or drivers may be programmed.

Optionally, mobile computing device 100 may access a server to download the conscious rhythmic breathing sensing application as one or more software products or computer program products associated with measuring, recording and presenting data recorded by sensors 40 or 41 and/or for configuring settings of any of sensors 40, 41, 400, 402, 410 and 412. The one or more computer program products may be provided in the form of a conscious rhythmic breathing sensing application which causes mobile computing device 100 or components thereof to execute instructions for measuring, recording and presenting data and/or for configuring settings of any of sensors 40, 41, 400, 402, 410 and 412. The instructions may further support a graphical user interface through which this user may review data and/or configure one or more user settings.

Furthermore, use of the breathing application can be free of cost or a paid service that has a subscription-based billing or a transaction-based billing, such as pay-per-use and pay-per-feature.

Regulating breathing parameters through mindful living facilitated by a conscious rhythmic breathing sensing device the user will experience reduced stress and healthier living.

While the present disclosure has been described in terms of example aspects, those skilled in the art will recognize that the present disclosure can be practiced with modifications in the spirit and scope of the appended claims. The examples given above are merely illustrative and are not meant to be an exhaustive list of all possible designs, aspects, applications or modifications of the present disclosure.

What is claimed is:

1. A system for increased breathing awareness, the system comprising:
    a first clip configured to grip an alar rim of a user nose;
    a first air deflection plate pivotably coupled with the first clip by a first hinge and the first air deflection plate being configured to, while the first clip is attached to the alar rim of the user nose, pivot relative to the first clip and to at least partially deflect air flow from or into a first nostril of the user nose and to produce a sound in response to the user exhaling while the first clip grips the alar rim of the user nose and the first air deflection plate is exterior to the first nostril;
    one or more sensors including at least one pressure sensor coupled with the first air deflection plate and configured to sense breathing and transmit data resulting from the sensed breathing; and
    a mobile computing device programmed to receive and process data transmitted by the one or more sensors into breathing feedback and to present the breathing feedback to an output of the mobile computing device.

2. The system as set forth in claim 1, further comprising:
    a second air deflection plate pivotably coupled with the first clip by a second hinge and configured to at least partially deflect air flow from or into a second nostril with the first clip gripping the user nose and the second air deflection plate exterior to the second nostril; and
    wherein the one or more sensors are also configured to sense breathing through the second nostril.

3. The system as set forth in claim 1, wherein the first air deflection plate comprises an irregular surface.

4. The system as set forth in claim 1, wherein the first air deflection plate comprises a corrugated surface.

5. The system as set forth in claim 1, wherein the first air deflection plate is configured to produce a sound in response to a user exhaling or inhaling.

6. The system of claim 1, wherein the first air deflection plate is configured to produce mechanical waves of pressure and displacement in air flow deflected by the first air deflection plate.

7. The system of claim 6, wherein the mechanical waves have a frequency in the range of from about 20 Hz to about 20,000 Hz.

8. The system of claim 1, wherein the one or more sensors are coupled to an upper surface of the first air deflection plate.

9. The system of claim 1, wherein the one or more sensors are coupled to a lower surface of the first air deflection plate.

10. The system of claim 1, wherein the one or more sensors are coupled to upper and lower surfaces of the first air deflection plate.

11. The system of claim 1, wherein the one or more sensors are embedded within the first air deflection plate.

12. The system as set forth in claim 1, wherein the mobile computing device is configured to present the breathing feedback by presenting one or more of average breathing volume, current breathing rate, average breathing rate, lung capacity, percentage of oxygen intake, comparisons between current breathing volume and previous or average breathing volume and comparisons between breathing rate and previous or average breathing rate.

13. The system as set forth in claim 1, wherein the first hinge is not a living hinge.

14. The system as set forth in claim 1, wherein the sound produced in response to the user exhaling is a swishing sound.

* * * * *